(12) United States Patent
Declercq et al.

(10) Patent No.: US 9,072,717 B2
(45) Date of Patent: Jul. 7, 2015

(54) COSMETIC COMPOSITIONS CONTAINING ALPHA GLUCOSIDASE INHIBITORS AND METHODS OF USE

(75) Inventors: Lieve Declercq, Ekeren (BE); Daniel H. Maes, Huntington, NY (US); Hugo A. Corstjens, Maaseik (BE)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 11/857,105

(22) Filed: Sep. 18, 2007

(65) Prior Publication Data

US 2009/0074822 A1 Mar. 19, 2009

(51) Int. Cl.
| | | |
|---|---|---|
| *A61K 36/06* | (2006.01) | |
| *A61K 36/185* | (2006.01) | |
| *A61K 36/22* | (2006.01) | |
| *A61K 8/41* | (2006.01) | |
| *A61K 8/49* | (2006.01) | |
| *A61K 8/97* | (2006.01) | |
| *A61Q 19/08* | (2006.01) | |

(52) U.S. Cl.
CPC .............. *A61K 36/22* (2013.01); *A61K 8/415* (2013.01); *A61K 8/4913* (2013.01); *A61K 8/4926* (2013.01); *A61K 8/97* (2013.01); *A61K 2800/782* (2013.01); *A61Q 19/08* (2013.01)

(58) Field of Classification Search
USPC .............................................. 424/401
See application file for complete search history.

(56) References Cited

U.S. PATENT DOCUMENTS

| | | | |
|---|---|---|---|
| 3,215,724 A | 11/1965 | Strobel et al. | |
| 3,439,088 A | 4/1969 | Edman | |
| 3,781,417 A | 12/1973 | Welters et al. | |
| 3,818,105 A | 6/1974 | Coopersmith et al. | |
| 4,116,984 A | 9/1978 | Prinzbach et al. | |
| 4,677,152 A | 6/1987 | Allen et al. | |
| 4,702,844 A | 10/1987 | Flesher et al. | |
| 4,720,353 A * | 1/1988 | Bell ............................... | 516/23 |
| 4,970,252 A | 11/1990 | Sakuta et al. | |
| 5,236,986 A | 8/1993 | Sakuta | |
| 5,412,004 A | 5/1995 | Tachibana et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,824,320 A * | 10/1998 | Rouillard et al. ............. | 424/401 |
| 5,837,793 A | 11/1998 | Harashima et al. | |
| 5,843,193 A | 12/1998 | Hawkins et al. | |
| 7,172,754 B1 * | 2/2007 | Rosevear et al. ................ | 424/59 |
| 7,935,673 B2 | 5/2011 | Kawaguchi et al. | |
| 2002/0051799 A1 | 5/2002 | Purche et al. | |
| 2004/0115153 A1 | 6/2004 | Yu | |
| 2005/0048008 A1 * | 3/2005 | Gupta ............................. | 424/59 |
| 2006/0034875 A1 | 2/2006 | Nakanishi et al. | |
| 2006/0099690 A1 | 5/2006 | Chang et al. | |
| 2006/0110415 A1 * | 5/2006 | Gupta ............................. | 424/401 |
| 2006/0159645 A1 * | 7/2006 | Miller et al. ................ | 424/70.12 |
| 2006/0165636 A1 * | 7/2006 | Hasebe et al. .............. | 424/70.14 |
| 2006/0292080 A1 * | 12/2006 | Abram et al. .................... | 424/45 |
| 2007/0092461 A1 * | 4/2007 | Gupta ............................. | 424/62 |
| 2007/0122493 A1 | 5/2007 | Funayama et al. | |
| 2007/0232698 A1 * | 10/2007 | Shibuya et al. ................ | 514/561 |
| 2008/0081837 A1 | 4/2008 | Piccirilli et al. | |
| 2010/0029918 A1 | 2/2010 | Kawaguchi et al. | |

FOREIGN PATENT DOCUMENTS

| | | |
|---|---|---|
| CN | 1726004 | 1/2006 |
| EP | 1674106 | 6/2006 |
| EP | 1840131 | 10/2007 |
| FR | 2851469 | 8/2004 |
| JP | 61018708 | 1/1986 |
| JP | 61-18708 | 4/1994 |
| JP | 09-048736 | 2/1997 |
| JP | 2001-163795 | 6/2001 |
| JP | 2002-255733 | 9/2002 |
| JP | 2002-267655 | 9/2002 |
| JP | 2004-168770 | 6/2004 |
| JP | 2005-082509 | 3/2005 |
| JP | 2006-176454 | 7/2006 |
| JP | 2006-188463 | 7/2006 |
| JP | 2008-501003 | 1/2008 |
| WO | WO2004/024798 | 3/2004 |
| WO | WO2005-032570 | 10/2004 |
| WO | 2007092312 A2 * | 2/2006 |
| WO | WO2006/067985 | 6/2006 |

OTHER PUBLICATIONS

200400611 I3, Jun. 2006, Derwent, Ayothi, V.*
"GNPD—Global New Products Database, Monitoring New Product Trend", Aqua Gel SOS-Yves Rocher Protectyl Vegetal (Aug. 2007) [Retrieved on Sep. 14, 2007] Retrieved from: http://www.gnpd.com/sinatra/gnpd/search_results/&item_id=748894, 2 pages.
"GNPD—Global New Products Database, Monitoring New Product Trend", Sun Lotion SPF 50-Yves Rocher Protectyl Vegetal (Jun. 2007) [Retrieved on Sep. 14, 2007] Retrieved from: http://www.gnpd.com/sinatra/gnpd/search_results/&item_id=725655, 2 pages.
"GNPD—Global New Products Database, Monitoring New Product Trend", Intensive Tanning Oil SPF 4-Yves Rocher Protectyl Vegetal (Jun. 2007) [Retrieved on Sep. 14, 2007] [Retrieved from: http://www.gnpd.com/sinatra/gnpd/search_results/&item_id=724696, 2 pages.
"GNPD—Global New Products Database, Monitoring New Product Trend", Anti-Wrinkle Face Tanning Cream-Yves Rocher Protectyl Vegetal (Jun. 2006) [Retrieved on Sep. 14, 2007] [Retrieved from: http://www.gnpd.com/sinatra/gnpd/search_results/&item_id=539747, 2 pages.

(Continued)

*Primary Examiner* — Chris R Tate
*Assistant Examiner* — Randall Winston
(74) *Attorney, Agent, or Firm* — Julie M. Blackburn

(57) ABSTRACT

A composition containing at least one alpha glucosidase inhibitor, and a method for ameliorating the adverse effects of aging and sun damage on keratinous surfaces such as skin by treating with a composition containing at least one alpha glucosidase inhibitor; as well as regimens and kits for treating skin.

23 Claims, No Drawings

(56) References Cited

OTHER PUBLICATIONS

"GNPD—Global New Products Database, Monitoring New Product Trend", SOS After Sun Gel-Yves Rocher Protectyl Vegetal (Jun. 2006) [Retrieved on Sep. 14, 2007] [Retrieved from: http://www.gnpd.com/sinatra/gnpd/search_results/&item_id=539163, 2 pages.

"GNPD—Global New Products Database, Monitoring New Product Trend", Hydra Protection Cream-Yves Rocher Protectyl Vegetal (Jun. 2006) [Retrieved on Sep. 14, 2007] [Retreived from: http://www.gnpd.com/sinatra/gnpd/search_results/&item_id=539768, 2 pages.

"GNPD—Global New Products Database, Monitoring New Product Trend", Spray Hidra-Protection + 15-Yves Rocher Protectyl Vegetal (Jul. 2006) [Retrieved on Sep. 14, 2007] [Retrieved from: http://www.gnpd.com/sinatra/gnpd/search_results/&item_id=560949, 2 pages.

"GNPD—Global New Products Database, Monitoring New Product Trend", Bio-Smoothing Tonic-La Colline Celular (Aug. 2007) [Retrieved on Aug. 28, 2007] [Retrieved from: http://www.gnpd.com/sinatra/gnpd/search_results/&item_id=759492, 2 pages.

"GNPD—Global New Products Database, Monitoring New Product Trend", Cellular Bio-Activating Gel-La Colline Celular (Jul. 2007) [Retrieved on Aug. 28, 2007] [Retrieved from: http://www.gnpd.com/sinatra/gnpd/search_results/&item_id=735683, 2 pages.

PCT International Search Report; International Application No. PCT/US2008/071484; Completion Date: Jan. 8, 2009; Dae of Mailing: Jan. 8, 2009.

PCT Written Opinion of the International Searching Authority, or the Declaration; International Application No. PCT/US2008/071484; Completion Date: Jan. 8, 2009; Mailing Date: Jan. 8, 2009.

Antille et al., "Decreased oxidative state in non-lesional skin of atopic dermatitis," Dermatology 204(1):69-71, 2002.

Avery et al., "The effects of the Maillard reaction on the physical properties and cell interactions of collagen," Pathol Biol (Paris) 54(7):387-95, 2006.

Baumer et al., "Highly selective phosphodiesterase 4 inhibitors for the treatment of allergic skin diseases and psoriasis," Inflammation & Allergy—Drug Targets 6:17-26, 2007.

Cohen et al., "Alpha-glucosidase inhibition prevents increased collagen fluorescence in experimental diabetes," Gen Pharmacol 22(4):607-10, 1991.

Ingber et al., "A novel treatment of contact dermatitis by topical application of phospholipase A2 inhibitor; a double-blind placebo-controlled pilot study," Int J Immunopathol Pharmacol 20(1):191-5, 2007.

Monnier et al., "Prevention and repair of protein damage by the Maillard reaction in vivo," Rejuvenation Res 9(2):264-73, 2006.

Muizzuddin et al., "Structural and functional differences in barrier properties of African American, Caucasian and East Asian skin," J Dermatol Sci 59(2):123-8, 2010.

Yoshikawa, et al.; Polyphenol Constituents from *Salacia* Species: Quantitative Analysis of Mangiferin with Glucosidase adn Aldose Reductase Inhibitory Activities; Yakugaku Zasshi; vol. 121; pp. 371-378; 2001.

Nonenzymic Glycation and Skin Aging; Edited by Guang yingjie; vol. 22; No. 6; pp. 243; paragraph 2); 2001.

* cited by examiner

COSMETIC COMPOSITIONS CONTAINING ALPHA GLUCOSIDASE INHIBITORS AND METHODS OF USE

TECHNICAL FIELD

The invention is in the field of cosmetic compositions for application to keratinous surfaces for ameliorating the adverse effects of aging or sun damage, or for purposes of treatment and beautification.

BACKGROUND OF THE INVENTION

Alpha glucosidase is an enzyme present in the body that hydrolyzes the α-1,4-glycosidic linkage of disaccharides and polysaccharides to form monosaccharides such as glucose, which can then be used for energy. While glucose and other monosaccharides are necessary for life, they can also cause undesired effects when they are not present in exactly the right amount. For example, it has long been known that monosaccharides such as glucose react with free amino groups on the skin surface to form certain intermediates that begin a cascade of reactions that ultimately results in an irreversible crosslinking of skin proteins such as collagen. Crosslinking of collagen in turn contributes to the wrinkling and senescence of skin with age. The metabolites generated during the reaction cascade are often referred to as advanced glycation endproducts (AGE). The AGE's are a heterogeneous and complex mixture of compounds that have been shown to play a role in skin aging. Further, it has been shown that individuals with diabetes have skin proteins with increased crosslinking when compared to non-diabetic individuals, presumably because the increased presence of glucose in their skin and body tissues results in formation of AGE in their skin. For that reason, if something inhibits the ingredients that contribute to formation of AGE's it will have a positive impact on the occurrence of skin protein crosslinking and its resulting negative effects on skin. One way to inhibit formation of AGE's in skin is to treat the skin with ingredients that inhibit α-glucosidase, so that the carbohydrates, disaccharides, and 1,4 polysaccharides on the skin surface are not readily metabolized into their constituent sugars. This in turn ensures that fewer such monosaccharides are present on the skin surface to contribute to the formation of AGE's.

Accordingly it is an object of the invention to provide a cosmetic composition for treating skin, or other keratinous surfaces such as nails or hair, containing at least one α-glucosidase inhibitor.

It is a further object of the invention to provide a composition for treating skin containing at least one α-glucosidase inhibitor, wherein said composition is substantially free of monosaccharides and/or other complex sugars capable of reducing to simple sugars such as glucose or sucrose or both.

It is a further object of the invention to provide a method for ameliorating the adverse effects of aging or sun damage on skin, or cosmetically treating skin for improvement, comprising applying to the skin a cosmetic composition containing at least one α-glucosidase inhibitor.

It is a further object of the invention to provide a skin treatment regimen or process comprised of treating skin with at least two products selected from cleanser, toner, and leave-on skin treatment composition, wherein at least one of the products used in the process contains at least one α-glucosidase inhibitor, and preferably, wherein at least one of the products is substantially free of monosaccharides, or di- or polysaccharides that contain at least one α-1,4-glycosidic linkage operable to hydrolyze, to form simple sugars or monosaccharides.

It is a further object of the invention to provide a kit for treating skin comprised of at least two products selected from cleanser, toner, and at least one leave on skin treatment composition wherein one or more, preferably all of the products are free of monosaccharides, or polysaccharides capable of hydrolyzing to form monosaccharides, and wherein at least one product in the kit components contains at least one α-glucosidase inhibitor.

SUMMARY OF THE INVENTION

The invention comprises a cosmetic composition for treating keratinous surfaces at least one α-glucosidase inhibitor.

The invention further comprises a method for ameliorating the adverse effects of aging or sun damage on keratinous surfaces such as skin comprising applying to the keratinous surface a composition comprising at least one α-glucosidase inhibitor.

The invention further comprises a regimen or process for treating skin comprising treating skin with at least two products selected from cleanser, toner, or leave on skin treatment composition, wherein at least one of the products used in the regimen contains at least one α-glucosidase inhibitor, and preferably, wherein at least one of the regimen products, preferably all, are substantially free of monosaccharides or di- or polysaccharides containing 1,4-α-glycosidic linkages that are operable to hydrolyze, to form simple sugars upon exposure to α-glucosidase.

The invention further comprises a kit for treating skin comprising at least two of: (i) a receptacle containing a cleanser, (ii) a receptacle containing a toner, and (iii) a receptacle containing a leave on skin treatment composition.

DETAILED DESCRIPTION

I. Definitions

A. The term "alpha glucosidase" or "α-glucosidase" means an enzyme that hydrolyzes the 1,4-α-glycosidic linkage of disaccharides and/or polysaccharides to form simple sugars or monosaccharides such as glucose.

B. The term "alpha glucosidase inhibitor" or "α-glucosidase inhibitor" means that the compound, molecule, extract, or polymer exhibits α-glucosidase inhibitory activity in an α-glucosidase assay based upon the following reaction:

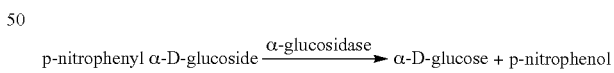

wherein the α-glucosidase activity is measured by the release of p-nitrophenol, and as further set forth in Example 1.

C. The term "ameliorating the adverse effects of aging or sun damage" means improving the appearance of skin conditions found in aging or sun damaged skin such as lines, wrinkles, laxity, age spots, uneven coloration or skin tone, blemishes, dryness, yellow or brownish discoloration, sun burn, cellulite or dimpled skin, and the like.

D. The term "liquid" means a composition that is pourable at room temperature (25° C.)

E. The term "nonvolatile" means that the ingredient has a vapor pressure of less than about 2 mm. of mercury at 20° C.

F. The term % means percent by weight of the total composition unless otherwise indicated.

G. The term "regimen" means a process for treating a keratinous surface that occurs in steps, preferably with multiple products. For example a skin treatment regimen may comprise the use of a skin cleanser, followed by application of a toner, then a skin serum cream or lotion. Alternatively, a skin treatment regimen may comprise use of a cleanser followed by a skin serum, cream or lotion, and so on.

H. The term "semi-solid" means a composition that deforms upon application of shear.

I. The term "solid" means a composition that is capable of being self-supporting at room temperature, which may be found in the molded or pressed forms such as sticks, cakes, pressed, and the like.

J. The term "substantially free of" means that the particular ingredient referred to is not present in an amount sufficient to require that it be listed on the ingredient labeling for the product when in compliance with the United States Food and Drug Laws, 21 C.F.R., Chapter I, Part 701.

K. The term "volatile" means that the ingredient has a vapor pressure of at least about 2 mm. of mercury at 20° C.

II. The Alpha Glucosidase Inhibitor

The composition of the invention comprises at least one alpha glucosidase inhibitor, preferably ranging from about 0.0001 to 75%, preferably from about 0.005 to 70%, more preferably from about 0.01 to 50% by weight of the total composition. Suitable alpha glucosidase inhibitors may be chemical compounds, botanical extracts, polymers, and the like.

A. Botanical Extacts

A number of extracts from plants such as vegetables, flowers, trees, fruits, and the like, exhibit alpha glucosidase inhibitory activity. Examples of such botanical extracts include those from the genus *Salacia, Connarus, Donella, Sapium, Zanthophyllum, Dimocarpus, Erythroxylon, Disopyros, Careya, Semecarpus, Calophyllum, Shorea, Duabanga, Cratoxylon, Arhidendron, Nauclea, Eupatorium, Hibiscus, Helicteres, Milletia, Brucea, Millettia, Sesbania, Barrington, Glycyrrhiza, Rumex, Myrtus, Taraxacum, Viscum, Ganoderma, Pinus, Penares, Origanum, Grifola, Sangzhi, Lobelia, Umbilicaria, Syzgium, Commelina, Salacia, Eucommia, Angylocalyx, Arachniodes*, and the like.

More specifically, botanicals such as *Salicia Reticulata* (*Salaretin*), *Connarus Cochinensis, Sapium Discolor, Zanthophyllum Annamense, Dimocarpus Longan, Erythroxylon Cambodianum, Diospyros Malabarica, Careya Arborea, Semecarpus Cochinchinensis, Calophyllum Calaba, Shorea Guiso, Duabanga Sonneratioides, Cratoxylon Formosum, Archidendron Turgidum, Nauclea Officinalis, Eupatorium Odoratum, Hibiscus Mesnyi, Milletia Diptera, Milletia Conraui, Ascophyllum Nodosum, Brucea Javanica, Mangifera Indicia, Sesbania Grandiflora, Glycyrrhiza Uralensis, Rumex Bucephalophorus, Murtex Communis, Taraxacum Officinale, Viscum Album, Ganoderma Lucidum, Pinus Densiflora, Penarus Schulzei, Origanum Majorana, Grifola Frondosa, Sangzhi* (*Ramulus Mori*), *Lobelia Chinensis, Touchi, Syzgium Aromaticum, Commelina Communis, Salacia Reticulata, Eucommia Ulmoides, Angylocalyx Boutiqueanus, Arachniodes Standishii*, or mixtures thereof are suitable.

B. Chemical Compounds

Also suitable as alpha glucosidase inhibitors are various types of compounds including, but not limited to those further set forth.

1. Substituted Arabinitols

Certain derivatives of arabinatol, preferably dideoxy derivatives may be suitable alpha-glucosidase inhibitors. More preferred are dideoxy arabinitol derivatives having imino substitutions. Most preferred is 1,4-dideoxy-1,4-imino-D-arabinitol (also referred to as DAB-1).

2. Piperidines

Also suitable are certain piperidine derivatives, including those substituted with hydroxyl C1-4 alkyl and/or hydroxyl groups. Preferably such piperidine derivatives are substituted with both methyl and/or ethyl hydroxyl alkyl and hydroxyl groups, and include Miglitol, which is (2R,3R,4R,5S)-1-(2-hydroxyethyl)-2-(hydroxymethyl) piperidine-3,4,5-triol.

3. Cyclohexenes

Also suitable are certain cyclohexene derivatives, for example those substituted with amino, hydroxyalkyl, or hydroxyl groups. More preferably, the cyclohexene derivatives are substituted with hydroxymethyl or hydroxyethyl substitutents and amino substitutuents. Most preferred is a cyclohexene derivative referred to as valienamine, which is (1S,2S,3R,6S)-6-Amino-4-(hydroxymethyl)-4-cyclohexene-1,2,3-triol.

Also suitable are cyclohexene derivatives as set forth in U.S. Pat. No. 4,116,984, hereby incorporated by references in its entirety. Such compounds include, but are not limited to conduramine, epistamine, streptamine, and the like.

Suitable cyclohexene derivatives also include voglibose, which is (1S,2S,3R,4S,5S)-5-(1,3-dihydroxypropan-2-ylamino)-1-(hydroxymethyl)cyclohexane-1,2,3,4-tetrol.

4. Other Compounds

Also suitable is acarbose, or (2R,3R,4S,5R,6R)-5-[(2R,3R,4S,5R,6R)-5-[(2R,3R,4S,5R,6R)-3,4-dihydroxy-6-methyl-5-[[(1S,4S,5S,6S)-4,5,6-trihydroxy-3-(hydroxylmethyl)-1-cyclohex-2-enyl]amino]oxan-2-yl]oxy-3,4-dihydroxy-6-(hydroxymethyl)oxan-2-yl]oxy-6-(hydroxymethyl)oxane-2,3,4-triol.

Sulfonamide substituted chalcones (aromatic ketones) may also be suitable for use as the alpha-glucosidase inhibtor. Such chalcones are substituted with one or more sulfonamide groups.

Another suitable material is caffeoylsophorose and its derivatives, such as 6-O-caffeoylsophorose.

Other examples of suitable materials include 4-methoxy-trans-trans-cinnamic acid; baicalein; glycosyl ureas; oleanic acid; 4,5,6,7-tetrachloro-N-cycloheptylphthalimide; acylated anthocyanins; luteoplin; amentoflavone; diadzein; bromoconduritol; tetrachlorophthalimide; or mixtures thereof.

III. Other Ingredients

The cosmetically acceptable compositions that may be suitable vehicles for the alpha glucosidase inhibitor may be anhydrous or aqueous based. If aqueous, the compositions may be in the emulsion form, e.g. water in oil or oil in water emulsion form, or in an aqueous gel. If present in the emulsion from, from about 0.01-99%, preferably from about 0.5-95%, more preferably from about 1-90% by weight of the total composition of water is present; and from about 0.01-98%, preferably from about 0.1-95%, more preferably from about 0.5-90% by weight of the total composition of oil is present. The composition may contain a variety of other ingredients including but not limited to those set forth herein.

A. Volatile Oils

1. Volatile Silicones

Suitable volatile oils generally have a viscosity ranging from about 0.5 to 5 centistokes 25° C. and include linear silicones, cyclic silicones, branched silicones, paraffinic hydrocarbons, or mixtures thereof.

Cyclic silicones are of the general formula:

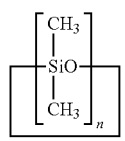

where n=3-6.

Linear volatile silicones in accordance with the invention have the general formula:

$(CH_3)_3Si-O-[Si(CH_3)_2-O]_n-Si(CH_3)_3$ where n=0, 1, 2, 3, 4, or 5, preferably 0, 1, 2, 3, or 4.

Branched volatile silicones are generally of the formula:

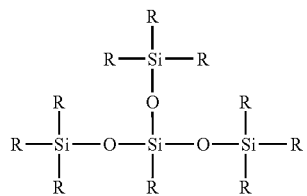

wherein R is $C_{1-4}$ alkyl, preferably methyl.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, dodecamethylcyclohexasiloxane and the like. Also suitable are linear volatile silicones such as hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof.

Suitable branched volatile silicones include methyl trimethicone, ethyl trimethicone, propyl trimethicone, butyl trimethicone and the like. Methyl trimethicone may be purchased from Shin-Etsu Silicones and has the trade name TMF 1.5, having the viscosity of 1.5 centistokes at 25° C.

2. Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference in their entireties for all purposes.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

B. Non-Volatile Oils

A variety of nonvolatile oils are also suitable for use in the cosmetic compositions of the invention. The nonvolatile oils generally have a viscosity of greater than about 5 to 10 centistokes at 25° C., and may range in viscosity up to about 1,000,000 centipoise at 25° C. Preferably, the nonvolatile oils are liquid. Further examples of nonvolatile oils include, but are not limited to:

1. Esters

Suitable esters are mono-, di-, and triesters. The composition may comprise one or more esters selected from the group, or mixtures thereof.

(a) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(b). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(c). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described on pages 1670-1676 of the C.T.F.A. Cosmetic Ingredient Dictionary and Handbook, Eighth Edition, 2000, which is hereby incorporated by reference in its entirety.

2. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Nonvolatile Silicones

Nonvolatile silicone oils, both water soluble and water insoluble, are also suitable for use in the composition. Such silicones preferably have a viscosity ranging from about 10 to 800,000 cst, preferably 20 to 200,000 cst at 25° C. Suitable water insoluble silicones include amine functional silicones such as amodimethicone; phenyl substituted silicones such as bisphenylhexamethicone, trimethylsiloxyphenyl dimethicone, phenyl trimethicone, or polyphenylmethylsiloxane; dimethicone, dimethicone substituted with $C_{2-30}$ alkyl groups such cetyl dimethicone.

Nonvolatile silicones may have the following general formula:

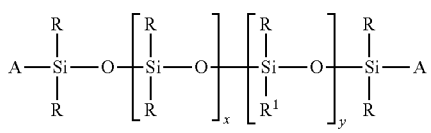

wherein R and R' are each independently $C_{1-30}$ straight or branched chain, saturated or unsaturated alkyl, phenyl or aryl, trialkylsiloxy, and x and y are each independently 0-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the tradenames Abil Wax 9801, or 9814.

C. Surfactants

The composition of the invention may contain one or more surfactants. The surfactants may be silicone or organic surfactants.

1. Silicone Surfactants

Suitable silicone surfactants include polyorganosiloxane polymers that have amphiphilic properties, for example contain both hydrophilic radicals and lipophilic radicals. These silicone surfactants may be liquids or solids at room temperature and include, but are not limited to those set forth herein.

(a). Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

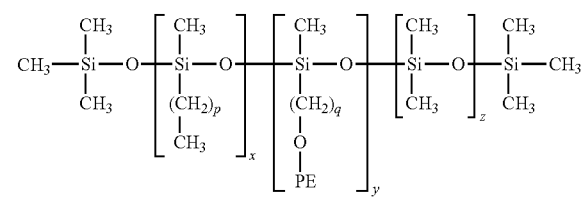

wherein p and q are from 0 to 40 (the range including all numbers between and subranges such as 2, 3, 4, 13, 14, 15, 16, 17, 18, etc.), and PE is $(—C_2H_4O)_a—(—C_3H_6O)_b—H$, wherein a is from 0 to 25, b is from 0 to 25, with the proviso that a and b cannot both be 0 simultaneously, wherein x, y and z are each independently ranging from 0 to 1 million, with the proviso that they cannot all be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Crosslinked Silicone Surfactants

Also suitable are various types of crosslinked silicone surfactants are referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer.

2. Organic Surfactants

The composition may contain one or more additional surfactants, such as nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula: where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula:

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

D. Oil Phase Structuring Agents

If desired, the composition may contain one or more oil phase structuring agents in the oil phase of the emulsion. The term "oil phase structuring agent" means an ingredient or combination of ingredients, soluble or dispersible in the oil phase, which will increase the viscosity, or structure, the oil phase. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

1. Silicone Structuring Agents

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to:

(a). Silicone Elastomers

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Coming's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossoplymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

(b). Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula

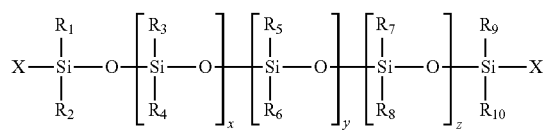

wherein: $R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

(c). Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bisstearyl dimethicone, which may be purchased from Gransil Industries under the tradename Gransil A-18, or behenyl dimethicone, behenoxy dimethicone.

2. Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

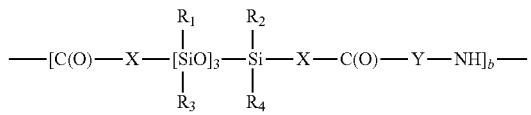

wherein, X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

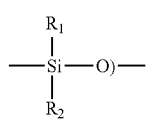

and Y is either:

(a) a linear or branched alkylene having from about 1-40 carbon atoms which may be substituted with (i) one or more amide groups having the general formula $R_1CONR_1$, or (ii) $C_{5-6}$ cyclic ring, or (iii) phenylene which may be substituted with one or more $C_{1-10}$ alkyl groups, or (iv) hydroxy, or (v) $C_{3-8}$ cycloalkane, or (vi) $C_{1-20}$ alkyl which may be substituted with one or more hydroxy groups, or (vii) $C_{1-10}$ alkyl amines; or (b) $TR_5R_6R_7$, wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

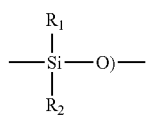

Preferred is where $R_1$, $R_2$, $R_3$, and $R_4$ are $C_{1-10}$, preferably methyl; and X and Y is a linear or branched alkylene. Preferred are silicone polyamides having the general formula

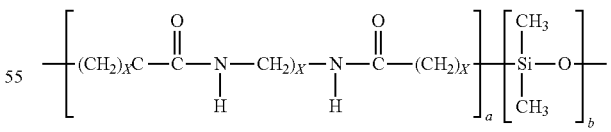

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

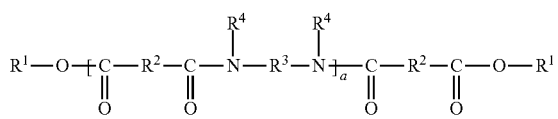

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a C30-42 hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

3. Natural or Synthetic Organic Waxes

Also suitable as the oil phase structuring agent may be one or more natural or synthetic waxes such as animal, vegetable, or mineral waxes. Preferably such waxes will have a higher melting point such as from about 60 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

4. Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

5. Silicas and Silicates

Another type of structuring agent that may be used in the oil phase of the composition is silica, silicates, or silica silylate, and alkali metal or alkaline earth metal derivatives thereof. These silicas and silicates are generally found in the particulate form and include silica, silica silylate, magnesium aluminum silicate, and the like.

E. Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols in monomeric or polymeric form such as polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Preferably, the humectants used in the composition of the invention are $C_{1-6}$, preferably $C_{2-4}$ alkylene glycols, most particularly butylene glycol.

F. Aqueous Phase Structuring Agents

If the compositions of the invention contain an aqueous phase it may be desirable to include one or more aqueous phase structuring agents in the composition. Such agents will typically thicken or increase the viscosity of the aqueous phase. If present, suggested ranges are from about 0.01 to 30%, preferably from about 0.1 to 20%, more preferably from about 0.5 to 15% by weight of the total composition. Examples of such agents include various acrylate based thickening agents, natural or synthetic gums, and the like.

1. Acrylate Polymers

For example, acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

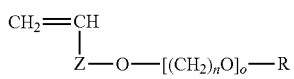

wherein Z is —$(CH_2)_m$; wherein m is 1-10, n is 2-3, o is 2-200, and R is a $C_{10\text{-}30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl(meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10\text{-}30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames.

Particularly suitable as the aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

2. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

G. Additional Botanical Extracts

It may be desirable to include one or more botanical extracts in the compositions in addition to those botanical extracts that have alpha-glucosidase inhibitory activity. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, padica pavonica extract, thermus thermophilis ferment extract, camelina sativa seed oil, boswellia serrata extract, olive extract, aribodopsis thaliana extract, acacia dealbata extract, acer saccharinum (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and the like. Further specific examples include, but are not limited to, *Glycyrrhiza Glabra, Salix Nigra, Macrocycstis Pyrifera, Pyrus Malus, Saxifraga Sarmentosa, Vilis Vinifera, Morus Nigra, Scutellaria Baicalensis, Anthemis Nobilis, Salvia Sclarea, Rosmarinus Officianalis, Citrus Medica Limonum, Panax Ginseng*, and mixtures thereof.

H. Sunscreens

It may also be desirable to include one or more sunscreens in the compositions of the invention. Such sunscreens include chemical UVA or UVB sunscreens or physical sunscreens in the particulate form.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula

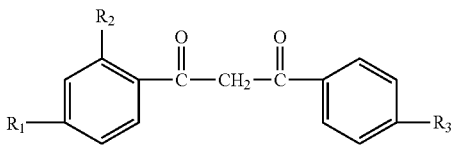

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

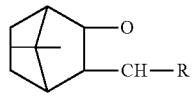

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

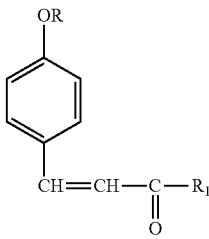

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula: wherein R through $R_9$ are each independently H, OH, $NaO_3S$, $SO_3H$, $SO_3Na$, Cl, R'', OR'' where R'' is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

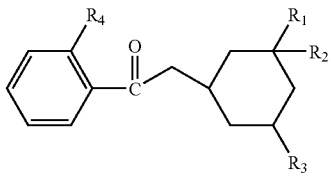

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

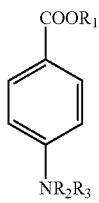

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art. Preferably, the claimed compositions have SPF values greater than 4.

I. Particulate Materials

The compositions of the invention may contain particulate materials in the form of pigments, inert particulates, or mixtures thereof. If present, suggested ranges are from about 0.1-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmentatious powders. Suitable non-pigmentatious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

J. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

K. Vitamins and Antioxidants

The compositions of the invention, may contain vitamins and/or coenzymes, as well as antioxidants. If so, 0.001-10%, preferably 0.01-8%, more preferably 0.05-5% by weight of the total composition are suggested. Suitable vitamins include ascorbic acid and derivatives thereof, the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

In one embodiment of the invention the composition is substantially free of glucose. In another embodiment of the invention the composition is substantially free of monosaccharides such as trioses such as aldotriose (glyceraldehyde) or ketotriose (dihydroxyacetone); tetroses such as aldotetrose (ethyrose or threose), or ketotetrose (erythrose); pentoses such as aldopentose (arabinose, lyxose, ribose, or xylose) or ketopentoses (ribulose or xylulose); hexoses such as aldohexoses (allose, altrose, galactose, glucose, gulose, idose, mannose, or talose), or ketohexoses (fructose psicose, sorbose, tagatose); heptoses such as keto-heptoses (mannoheptulose, sedoheptulose); octoses (octolose, 2-keto-3-deoxy-mannooctonate); or nonoses (sialose).

In another embodiment of the invention the composition is substantially free of glucose or other monosaccharides, or disaccharides or polysaccharides containing 1,4-alpha glycosidic linkages that are operable to hydrolysis to form monosaccharides.

In the embodiment where the compositions are substantially free of disaccharides containing 1,4-alpha glucosidic linkages, such disaccharides are sucrose, lactose, trehalose, cellobiose, mannobiose, or maltose.

In the embodiment wherein the compositions are free to polysaccharides containing sugars linked by 1,4-alpha glucosidic linkages, the polysaccharides are xanthan gum, gellan gum, dextrin, dextrain, cellulose, and the like.

IV. The Cosmetic Compositions

The cosmetic compositions of the invention may be found in a variety of forms, such as skin creams or lotions, or color cosmetic compositions such as foundation makeup, mascara, lip color, blush, eyeshadow, and the like. If in the emulsion form, the alpha glucosidase inhibitor may be found in the water phase or the oil phase of the emulsion depending on the type of derivative. For example, certain alpha glucosidase inhibitors may be hydrophilic and water soluble and will generally be found in the water phase of the emulsion. Certain other alpha glucosidase inhibitors may be lipophilic in nature and will more likely be found in the oil phase of the emulsion when the composition of the invention is in emulsion form.

Typical skin creams or lotions comprise from about 5-98% water, 1-85% oil, and from about 0.1 to 20% of one or more surfactants. Preferably the surfactants are nonionic and may be in the form of silicones or organic nonionic surfactants.

Typical color cosmetic compositions such as foundations, blush, eyeshadow and the like will preferably contain from about 5-98% water, 1-85% oil, and from about 0.1 to 20% of one or more surfactants in addition to from about 0.1 to 65% of particulates that are pigments or a combination of pigments and powders.

Typical mascara compositions generally contain from about 5-98% water, 1-85% oil, and from about 0.1 to 20% surfactant in addition to natural or synthetic polymers that are film forming, such as aqueous dispersions of acrylic copolymers, aqueous dispersions of polyurethane, or silicone resins.

Suitable lipsticks generally comprise from about 0.1-95% oil, from about 0.1-80% of a structuring agent, preferably an oil phase structuring agent, and from about 0.1-50% particulates, preferably a mixture of pigments and powders.

Typical toner compositions are generally comprised of about 0.1-99% water, from about 0.1-80% of humectants, and optionally other ingredient such as alpha or beta hydroxy acids, botanicals, and the other ingredients as set forth herein and in the specified ranges. Toners are most often used after cleansing and applied with a cotton pad to cleanse skin after cleansing.

Typical cleansing composition generally comprise from about 0.1-99% water, from about 0.1-85% surfactants, preferably foaming or cleansing surfactants, and possibly other conditioning ingredients such as humectants, botanicals, and the like. Typical cleansing surfactants are anionic, amphoteric, or zwitterionic surfacatants as set forth herein.

Serums are also suitable, and are generally in the aqueous gel or solution form containing water and ingredients such as aqueous phase thickening agents, botanicals, and the like. Suitable ranges of ingredients are from about 0.1-90%, preferably from about 0.5-85%, more preferably from about 5-85% water and from about 0.001-50% aqueous phase thickening agents, with the amounts of ancillary ingredients as set forth herein and in the same general percentage ranges.

V. Methods and Regimens

The composition of the invention may be applied in a regimen or process. For example, the composition of the invention may be in the form of a cleanser, toner, or leave on skin treatment composition such as serum, cream or lotion. In that case the alpha glucosidase inhibitor may be incorporated into any one, two, or all three of the different components. It is possible that the alpha glucosidase inhibitor may be found in the cleanser such that when the user cleans her skin and rinses off the cleanser residues of the alpha glucosidase inhibitor will remain on the skin. Alternatively, the alpha glucosidase inhibitor may be incorporated into a toner composition that is part of the regimen. In that case, when the toner is applied to skin with a cotton pad or similar, the alpha glucosidase inhibitor will remain on the skin surface. It is also possible for the alpha glucosidase inhibitor to be found in the skin cream or lotion portion of the regimen. In that case the alpha glucosidase inhibitor will remain on the skin when applied in the form of the skin cream or lotion.

The various products in the regiment may also be found in a kit form. The kit may contain the cleanser, toner, and leave on skin treatment composition. Alternatively the kit may contain only two of the products selected from cleanser, toner, and leave on skin treatment composition.

In one preferred embodiment, one or more of the products in the regimen or kit contain the alpha-glucosidase inhibitor, and one or more of the products in the kit are also substantially free of glucose, monosaccharides, or di- or polysaccharides that contain 1,4-alpha glycosidic linkages that are operable to hydrolysis into simple sugars upon exposure to the alpha glucosidase inhibitor.

The composition containing the alpha glucosidase inhibitor may be applied to the keratinous surface, preferably skin, from one to five times per day. Preferably, the composition is applied two to three times per day. Most often the skin will be treated in the morning with a day cream, and again at night with a night cream. Cleansing and toning products may also be incorporated into the treatment process.

The invention will be further described in connection with the following examples which are set forth for the purposes of illustration only.

EXAMPLE 1

The alpha glucosidase inhibitory activity of various plant extracts that may be used in the methods, compositions, and kits of the invention are as follows:

| | | Methanol extraction (A) | | Ethyl acetate extraction (B) | | Ethyl acetate extraction after heptane extraction (C) | | Methanol extraction of C. (D) | |
|---|---|---|---|---|---|---|---|---|---|
| | | % alpha glucosidase inhibition at (µg/ml) | | | | | | | |
| Genus | Species | 20 | 2 | 20 | 2 | 20 | 2 | 20 | 2 |
| *Connarus* | *cochinchinensis* | 84 | 4 | 100 | 65 | 100 | 28 | 98 | 94 |
| *Donella* | *lanceolata* | 8 | * | 98 | 5 | 10 | * | 100 | 44 |
| *Sapium* | *discolor* | 89 | 14 | 100 | 63 | 88 | 0 | 93 | 77 |
| *Xanthophyllum* | *annamense* | 0 | * | 4 | * | 14 | * | 0 | * |
| *Dimocarpus* | *Longan* | 0 | 0 | 16 | 7 | 14 | * | 0 | * |
| *Erythroxylon* | *cambodianum* | 66 | 6 | 3 | 0 | 23 | 6 | 99 | 87 |
| *Disopyros* | *malbarica* | 0 | 0 | 7 | 9 | 4 | 0 | 99 | 18 |
| *Careya* | *arborea* | 43 | 0 | 100 | 0 | 0 | 0 | 100 | 85 |
| *Semecarpus* | *Cochinchinensis* | 0 | 0 | 54 | 8 | 31 | 0 | 93 | 12 |
| *Calophyllum* | *calaba* | 4 | 0 | 100 | 29 | 78 | 18 | 98 | 38 |
| *Shorea* | *guiso* | 0 | 0 | 100 | 24 | 100 | 14 | 100 | 73 |
| *Duabanga* | *sonneratioides* | 100 | 86 | 100 | 91 | 100 | 82 | 94 | 97 |
| *Cratoxylon* | *formosum* | 40 | 7 | 100 | 29 | 78 | 18 | 98 | 38 |
| *Archidendron* | *turgidum* | 0 | 0 | 0 | 0 | 6 | 8 | 0 | 0 |
| *Nauclea* | *officinalis* | 0 | 0 | 47 | 4 | 17 | 3 | 100 | 44 |
| *Eupatorium* | *odoratum* | 0 | 0 | 0 | 0 | 5 | 6 | 0 | 0 |
| *Hibiscus* | *mesnyi* | 0 | 0 | 7 | 10 | 26 | 10 | 72 | 7 |
| *Helicteres* | *hirsuta* | 0 | 0 | 0 | 0 | 0 | 0 | 0 | 0 |
| *Milletia* | *diptera* | 24 | 0 | 29 | 13 | 13 | 0 | 54 | 16 |
| *Brucea* | *javanica* | 0 | 0 | 11 | 0 | 24 | 8 | 0 | 0 |

Materials were tested for alpha glucosidase inhibitory activity as follows:

Materials: Standard laboratory equipment, 96 well half area plates with UV transparent bottom (Costar, 3679), 8 channel multi pipette (20 to 200 µl), and spectrophotometer, Spectra Max Plus (Molecular Devices).

Reagents:
(a) Distilled water
(b) Potassium dihydrogen phosphate
(c) Dimethylsulfoxide (Acros, 12779)
(d) α-glucosidase—Saccharomyces cerevisiae recombinant (min. 125 U/mg protein) (Sigma, G0660)
(e) p-nitrophenol-α-D-glucopyranoside (Sigma, N1377)
(f) Australine hydrochloride, castanospermum australe (Calbiochem, #189422) (reference inhibitor)

Solution Preparation:
142 mM potassium phosphate buffer at pH 6.8
14.2 mM potassium phosphate buffer at pH 6.8
1.5 mM p-nitrophenyl-α-D-glucoside in 14.2 mM potassium phosphate (substrate solution) (note that 20 µl of substrate is needed for each well)
5 mU/ml of α-glucosidase in water (1 Unit will liberate 1.0 µmole of D-glucose from p-nitrophenyl-α-D-glucoside per minute at pH 6.8 at 37° C.) (note that 20 µL of enzyme solution (GLU3) is needed for each well)
1.3 mM of Australine HCl (reference inhibitor) in 142 mM potassium phosphate (using this stock solution, the end concentration of Australine in the well is 0.8 mM, which should cause about 50% inhibition in the well. 60 µl of reference inhibitor is needed per well)

Sample Preparation:
Stock solution of the test sample is prepared using 142 mM potassium phosphate buffer (solubility of test sample can be improved using DMSO/potassium phosphate mixtures. The end concentration of DMSO should not exceed 1% v/v which corresponds to 1.66% DMSO in the sample stock solution.

Procedure:
Pipette in each well 20 µl of the substrate solution and 60 µl of the potential inhibitor solutions. Equilibrate for 5 minutes at room temperature (25° C.).

Pipette with 8 channel multi-pipette 20 µl of the enzyme and mix well. The end concentration for substrate and glucosidase are 0.3 mM and 1 mU/ml, respectively. The absorbance was measured at 200 nM.

Calculation:
For each concentration of potential inhibitor, the initial reaction velocity is calculated, being the initial slope of the absorbance vs. time data.

The initial reaction velocity is plotted as a function of the concentration of potential inhibitor. The $IC_{50}$ value corresponds to the concentration of inhibitor that results in a 50% reduction in the initial velocity.

EXAMPLE 2

Compositions of the invention were made as follows:

| Ingredient | Eye Cream | Skin Lotion | Skin Cream |
|---|---|---|---|
| Aminoguanidine HCl | 0.10 | 0.20 | 0.20 |
| Wheat (*triticum vulgare*) bran extract/Olive (*olea europa*) extract | | 0.20 | 0.20 |
| *Selaginella Tamariscina* (Spike Moss) extract | 0.09 | 0.05 | 0.05 |
| Steareth-21 | 0.30 | 0.40 | 0.50 |
| FD&C Red No. 4 | 0.0002 | 0.0005 | 0.0008 |
| D&C Yellow No. 10 | | 0.001 | 0.0006 |
| Water/sodium hydroxide | | 0.01 | |
| Aminopropyl ascorbyl phosphate | 0.05 | 0.05 | 0.05 |
| Caprylic/capric triglyceride/*laminaria ochroleuca* extract | | 0.50 | |
| Caprylic/capric/myristic/stearic triglyceride | | 4.00 | |
| Cholesterol | 0.20 | 0.20 | 0.10 |

-continued

| Ingredient | Eye Cream | Skin Lotion | Skin Cream |
|---|---|---|---|
| Mica/titanium dioxide/polymethy methacrylate/triethoxycaprylyl silane | | 0.10 | 0.10 |
| Water/butylene glycol/decarboxy carnosine HCl (Alistin) | 0.10 | 0.10 | 0.10 |
| Barium sulfate | | 1.00 | 1.00 |
| Ammonium acrylodimethyltaurate/VP copolymer | | 0.50 | 1.35 |
| Acrylamide/sodium acryloyldimethyltaurate copolymer/isohexadecane/polysorbate 80 | | 0.70 | 0.80 |
| Glyceryl stearate/PEG-100 stearate | | 3.50 | |
| PEG-100 stearate | | | 1.50 |
| BHT | 0.05 | | |
| Creatine | | 0.50 | 0.50 |
| Titanium dioxide/mica/silica | 1.20 | 0.55 | 0.55 |
| Silica/titanium dioxide/dimethicone | | 0.25 | 0.25 |
| Pentaerythrityl tetraoctanoate | | 2.00 | 1.00 |
| Behenyl alcohol | | | 1.50 |
| Dimethicone/dimethicone silylate | 3.00 | | |
| Aminomethyl propanol | 0.32 | | |
| Ethylhexyl methoxycinnamate/silica/PVP | 10.00 | | 10.00 |
| Adenosine phosphate | 0.20 | 0.20 | 0.20 |
| Caprylyl glycol | | 0.70 | |
| Caprylyl glycol/phenoxyethanol/hexylene glycol | | | 0.50 |
| Tromethane | | | 0.125 |
| Zeolite | 0.50 | 0.50 | 1.00 |
| Cyclopentasiloxane/polysilicone-11/dimethicone | 2.00 | | |
| Phenoxyethanol | 0.59 | 0.62 | 0.52 |
| Disodium EDTA | 0.20 | 0.10 | 0.10 |
| Water/acetyl hexapeptide-8 | | 0.10 | 0.10 |
| Squalane/*hordeum vulgare* (barley) extract/*triticum vulgare* (wheat) germ extract | 0.20 | | |
| Pentylene | 1.50 | | |
| Cetyl esters | 3.00 | | |
| Jojoba esters | | 4.50 | |
| Dimethicone | 0.50 | 1.50 | 0.75 |
| Linoleic acid | 0.20 | | 0.20 |
| Butylene glycol | 6.00 | 5.03 | 4.00 |
| Butylene glycol/*oryza sativa* (rice) bran extract | | 0.20 | 0.20 |
| Mangiferin | 0.50 | | |
| *Connarus cochinchinensis* | | 0.50 | |
| Salaretin | | | 0.50 |
| Polyglyceryl-2 triisostearate | | 0.50 | 3.00 |
| Glyceryl stearate | | | 1.50 |
| Glyceryl polymethacrylate/PEG-8/palmitoyl oligopeptide | | 0.50 | 0.50 |
| Acetyl carnitine HCl | 0.01 | 0.05 | 0.05 |
| Yeast extract | | 0.50 | 0.50 |
| Water/glycerin/hesperidin methyl chalcone/steareth-20/dipeptide-2/palmitoyl tetrapeptide-7 | 1.00 | | |
| Water/glycosaminoglycans | 1.00 | | |
| *Vitis Vinifera* (grape) seed extract | 0.05 | 0.05 | 0.05 |
| Sodium dehydroacetate | 0.10 | 0.0001 | |
| Avobenzone | 3.00 | 3.00 | 3.00 |
| Acrylates/C10-30 alkyl acrylate crosspolymer | 0.08 | | |
| Cetearyl alcohol/cetearyl glucoside | 3.50 | | |
| Tocopheryl acetate | | 0.50 | 0.50 |
| Linoleic acid/linolenic acid | | 0.20 | |
| Trioctyldodecyl citrate | 0.50 | | |
| Carbomer | 0.20 | | |
| Creatine | 0.50 | | |
| Caffeine | 0.20 | 0.18 | 0.18 |
| Sodium hyaluronate | 0.02 | 0.02 | 0.02 |
| Benzophenone-3 | 2.00 | 2.00 | 5.00 |
| Water/lecithin/micrococcus lysate | | 0.50 | 0.05 |
| Trifluoro C-14 alkyl dimethicone | | 0.20 | 0.20 |
| Dimethicone | | 3.00 | 0.75 |
| Butylene glycol/PEG-8/*Bupleurum falcatum* root extract/caffeine/coenzyme A | 0.20 | | |
| *Polygonum cuspidatum* root extract (resveratrol) | 0.001 | 0.05 | 0.05 |
| Shea butter | 6.00 | 3.00 | |
| Ethylhexyl methoxycinnamate/laureth-4/laureth-23/tridecyl trimellitate | 6.15 | 6.15 | 6.15 |
| Oryzanol | 0.01 | | |
| Chlorophenesin | | | 0.20 |
| Potassium sorbate | | 0.20 | 0.20 |
| Polyethylene | | 0.75 | 0.50 |
| Petrolatum | | | 2.00 |
| N-acetyl-L-cysteine | 0.01 | | |
| Polyethylene | 1.00 | | |
| Water | QS | QS | QS |
| Phytosphingosine | 0.10 | 0.10 | 0.10 |

The compositions were prepared by combining the oil and water phases separately, the mixing well to emulsify.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An emulsion skin care cosmetic composition comprising effective amounts of at least one extract from the genus *Mangifera*, at least one extract from the genus *Ganoderma*, at least one extract from the genus *Rosmarinus*, at least one extract from the genus *Olea*, and an extract from *Selaginella tamariscina*, wherein the composition does not comprise a polymeric polyamide.

2. The composition of claim 1 which is an oil in water emulsion.

3. The composition of claim 1 which is substantially free of glucose.

4. The composition of claim 1 which is free of an ingredient selected from (i) monosaccharides, (ii) disaccharides containing 1,4-alpha glycosidic linkages, (iii) polysaccharides comprising 1,4-alpha glycosidic linkages; and (iv) mixtures thereof.

5. The composition of claim 1 further comprising glycerin.

6. The composition of claim 1, wherein the extract from *Mangifera* is *Mangifera Indica*.

7. The composition of claim 1, wherein the extract from the *Ganoderma* genus is *Ganoderma Lucidum*.

8. The composition of claim 1, wherein the extract from the genus *Rosmarinus* is from *Rosmarinus officianalis* and the extract from the genus *Olea* is from *Olea Europa*.

9. The composition of claim 8 further comprising dimethicone.

10. The composition of claim 1, wherein
the extract from the genus *Mangifera* is from *Mangifera Indicia*,
the extract from the genus *Ganoderma* is from *Ganoderma Lucidum*,
the extract from the genus *Rosmarinus* is from *Rosmarinus Officianalis*,
the extract from the genus *Olea* is from *Olea Europa*, and
wherein the composition further comprising yeast extract.

11. The composition of claim 10 further comprising glycerin.

12. The composition of claim 11 further comprising dimethicone.

13. The composition of claim 12 further comprising butylene glycol.

14. The composition of claim 13 which is a liquid emulsion.

15. The composition of 13 is in the form of an oil in water emulsion.

16. The composition of claim 1, wherein the composition is in the form of a serum.

17. The composition of claim 1 further comprising at least one silicone elastomer.

18. The composition of claim 17, wherein the silicone elastomer is selected from the group consisting of dimethicone/vinyl dimethicone crosspolymer, lauryl dimethicone/vinyl dimethicone crosspolymer, and mixtures thereof.

19. The composition of claim 1 further comprising a silicone gum having a viscosity ranging from about 500,000 to 100 million centistokes at 25° C.

20. The composition of claim 1 further comprising at least one glyceryl ester of a fatty acid or ethoxylated fatty acid.

21. The composition of claim 1, wherein glyceryl ester of the fatty acid or ethoxylated fatty acid is a PEG glyceryl stearate, polyglyceryl stearate, polyglyceryl isostearate, polyglyceryl ricinoleate, glyceryl trioctanoate, glyceryl linoleate, glyceryl myristate, PEG glycerol oleate, or mixtures thereof.

22. The composition of claim 1 further comprising Polysilicone-11.

23. The composition of claim 1 further comprising at least one polyoxyalkylenated or polyglycerolated silicone elastomer.

* * * * *